United States Patent [19]

Johnson et al.

[11] Patent Number: 5,220,064
[45] Date of Patent: Jun. 15, 1993

[54] SUBSTITUTED 4'-HYDROXYPHENYLACETIC ACID DERIVATIVES HAVING ANTIINFLAMMATORY AND ANALGESIC ACTIVITY

[75] Inventors: Graham Johnson, Ann Arbor, Mich.; Michael F. Rafferty, N. Branford, Conn.

[73] Assignee: Warner-Lambert Company, Morris Plains, N.J.

[21] Appl. No.: 327,283

[22] Filed: Mar. 22, 1989

Related U.S. Application Data

[63] Continuation of Ser. No. 935,358, Nov. 26, 1986, abandoned.

[51] Int. Cl.$^5$ ............................................. C07C 233/04
[52] U.S. Cl. ..................... 564/170; 564/158; 548/253; 554/51; 554/116
[58] Field of Search ............... 564/170, 158; 514/622, 514/558, 559; 548/253; 554/51, 116; 574/616, 381

[56] References Cited

U.S. PATENT DOCUMENTS

| | | | |
|---|---|---|---|
| 3,268,582 | 8/1966 | Zelle et al. | 260/559 |
| 3,282,939 | 11/1966 | Spivack et al. | 260/247.7 |
| 4,448,730 | 5/1984 | Van't Riet et al. | 260/500.5 H |
| 4,579,866 | 4/1986 | Stevenson et al. | 514/539 OR |

FOREIGN PATENT DOCUMENTS

| | | | |
|---|---|---|---|
| 626897 | 1/1963 | Belgium . | |
| 54174 | 6/1982 | European Pat. Off. . | |
| 206690 | 12/1986 | European Pat. Off. | 564/170 |
| 1959898 | 6/1970 | Fed. Rep. of Germany | 564/170 |
| 2526 | 1/1963 | France | 514/622 |
| 1336388 | 7/1963 | France . | |
| 128665 | 8/1982 | Japan | 564/170 |

OTHER PUBLICATIONS

Ott et al, Liedigs Ann., 425, pp. 314–337 (1921).
Szolesanyi et al, Arzneim.-Forsch, 25, No. 12 pp. 1877–1881 (1975).

*Primary Examiner*—Richard L. Raymond
*Assistant Examiner*—Shailendra Kumar
*Attorney, Agent, or Firm*—Joan Thierstein; Ronald A. Daignault

[57] ABSTRACT

The present invention is novel compounds, which are derivatives of 4'-hydroxyphenylacetic acid having antiinflammatory activity for the treatment of arthritis, asthma, Raynaud's disease, inflammatory bowel disorders, trigeminal or herpetic neuralgia, inflammatory eye disorders, psoriasis, and having analgesic activity. Particularly, the analgesia may be useful for the treatment of dental pain and headache, especially vascular headache, such as migraine, cluster and mixed vascular syndromes, as well as nonvascular tension headache.

2 Claims, No Drawings

SUBSTITUTED 4'-HYDROXYPHENYLACETIC ACID DERIVATIVES HAVING ANTIINFLAMMATORY AND ANALGESIC ACTIVITY

This is a continuation of U.S. Ser. No. 06/935,358 filed Nov. 26, 1986 now abandoned.

BACKGROUND OF THE INVENTION

The present invention is novel compounds, which are of 4'-hydroxyphenylacetic acid having antiinflammatory activity for the treatment of arthritis, asthma, Raynaud's disease, inflammatory bowel disorders, trigeminal or herpetic neuralgia, inflammatory eye disorders, psoriasis, and having analgesic activity. Particularly, the analgesia may be useful for the treatment of dental pain and headache, especially vascular headache, such as migraine, cluster and mixed vascular syndromes, as well as nonvascular tension headache. Thus, the present invention is also a pharmaceutical composition comprising the novel compounds together with a pharmaceutically acceptable carrier or methods of use of such compounds for treatment of the above noted conditions.

Compounds related to capsaicin are well-known for antiinflammatory and analgesic activity. Particularly, phenylacetamide derivatives are disclosed in U.S. Pat. Nos. 4,579,866 and 4,424,205 for the treatment of allergy, asthma, or inflammatory conditions and as analgesics or antiirritants respectively. The present compounds differ from the previously disclosed phenylacetamides in that the substituents on the phenyl moiety of the previously disclosed compounds do not include or make obvious the substituents as defined in the present application.

SUMMARY OF THE INVENTION

The novel compounds of the present invention are of the formula

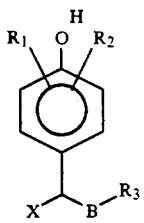

I and pharmaceutically acceptable salts thereof; wherein $R_1$ and $R_2$ are independently hydrogen, lower alkyl, OR', halogen, trifluoromethyl, nitro, $SCH_3$, $SO_2R'$, $SO_2NH_2$, $CO_2R'$, $CONR'R''$, CN, NHCOR', or tetrazolyl wherein R' and R'' are independently hydrogen or lower alkyl with the proviso that one of $R_1$ and $R_2$ cannot be hydrogen when the other is hydroxy and also both $R_1$ and $R_2$ cannot be hydrogen when $R_3$ is a linear or branched alkyl, alkynyl, or phenylalkyl, or a linear or branched alkenyl;

B is

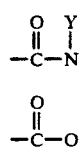 B₁

 B₂

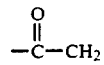 B₃

X and Y are independently hydrogen or lower alkyl; and $R_3$ is linear or branched $C_1$-$C_{18}$ alkyl; linear or branched $C_2$-$C_{18}$ alkenyl; linear or branched $C_2$-$C_{18}$ alkynyl; having each of the alkyl, alkenyl or alkynyl optionally substituted by OR', $CO_2R'$, CONR'R'', phenyl, naphthyl, or tetrazolyl wherein R' and R'' are independently as defined above; with the proviso that the alkyl is of from $C_8$-$C_{18}$ when substituted by OR' or phenyl.

DETAILED DESCRIPTION OF THE INVENTION

The term "lower alkyl" means a straight or branched hydrocarbon chain of from one to four carbon atoms, such as methyl, ethyl, propyl, butyl and isomers thereof.

The terms alkyl, alkenyl and alkynyl are hydrocarbon chains containing one or more saturated carbons; or two or more carbons having one or more double, or triple bonds, respectively.

The notations $C_1$-$C_{18}$, $C_2$-$C_{18}$, and $C_8$-$C_{18}$ indicate the number of carbons in the alkyl, alkenyl or alkynyl chain straight or branched.

The term "halogen" means chloro, bromo, fluoro.

Preferred embodiments of the present invention are of the formula H

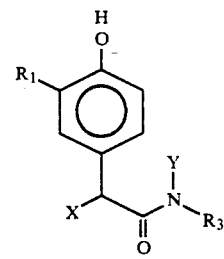 I₁ wherein $R_1$ is halogen, X and Y are hydrogen and $R_3$ is alkyl of $C_8$-$C_{18}$ optionally substituted as defined above.

More preferred embodiments are of the formula $I_1$ wherein $R_1$ is halogen, X and Y are hydrogen and $R_3$ is alkyl of $C_8$-$C_{18}$.

Most preferred embodiments are of the formula $I_1$ wherein $R_1$ is halogen, X and Y are hydrogen and $R_3$ is —$(CH_2)_7CH_3$.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as acetic, fumaric and the like or methanesulfonic acid, benzenesulfonic acid, p-toluenesulfonic acid, and the like, giving the hydrochloride, sulfate, acetate, fumarate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine tris(hydroxymethyl)aminomethane; and the like. (See for example, "Pharmaceutical Salts," *J. Pharm. Sci.* 66(1):1–19 (1977).)

The compounds of the invention may contain an asymmetric carbon atom. Thus, the invention includes the individual stereoisomers, and the mixtures thereof. The individual isomers may be prepared or isolated by methods known in the art.

The novel processes of the present invention may be shown, generally, as follows:

Generally, the preparation of the formula I wherein B is $B_1$, $B_2$ and $B_3$ is as shown in the following Schemes I, II and III, respectively.

Scheme I

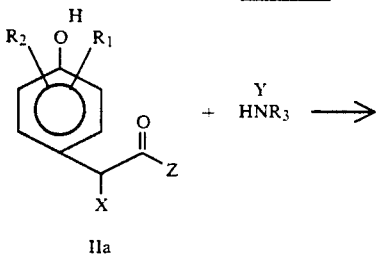

IIa

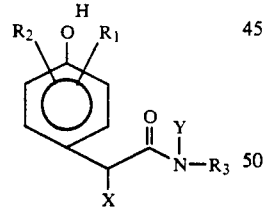

wherein $R_1$, $R_2$, X, Y and $R_3$ are as defined above and Z is a leaving group. The leaving group is as known to an ordinarily skilled artist such as, for example, chlorine, OR' wherein R' is as defined above,

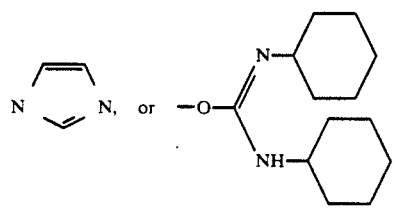

Scheme II

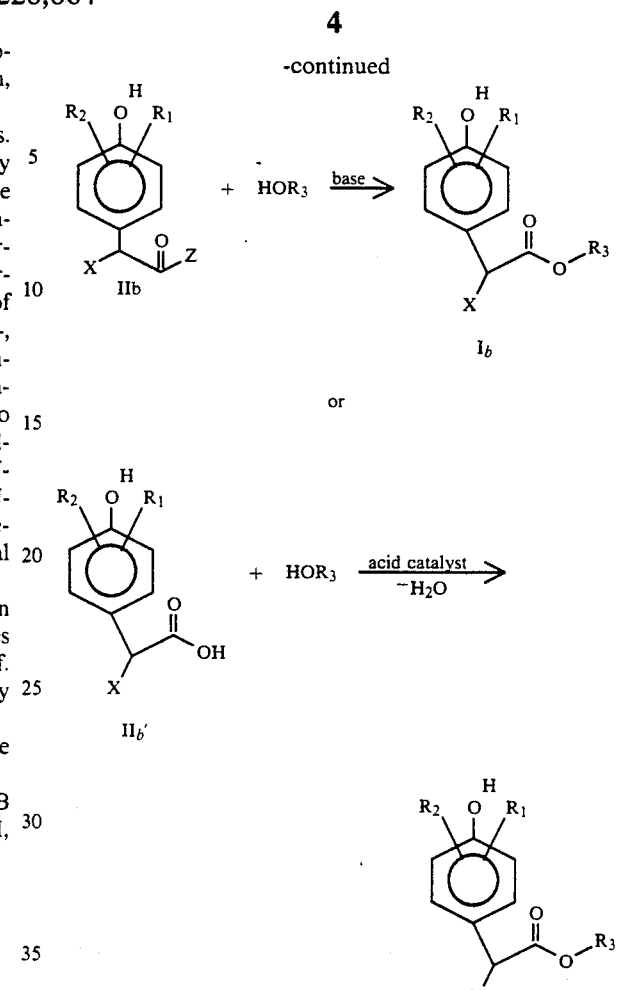

wherein $R_1$, $R_2$, X, $R_3$ and Z are defined above.

Scheme III

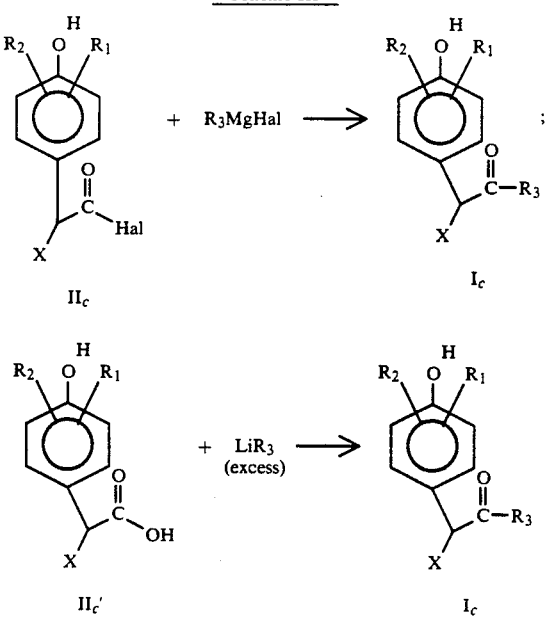

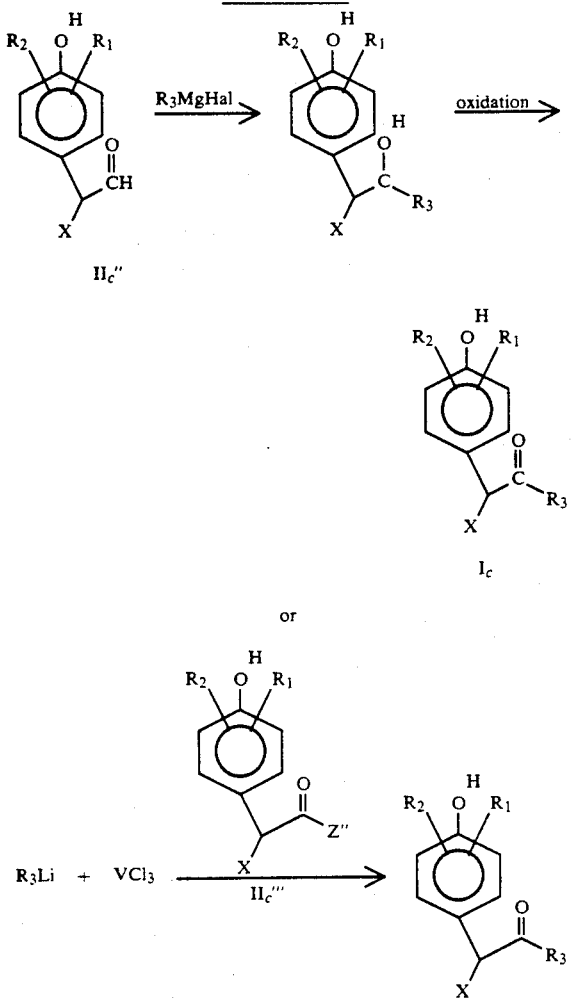

-continued
Scheme III wherein Z" is hydrogen or Hal and R₁, R₂, X, R₃ and Hal are as defined above.

The preparation of the above Schemes use standard synthetic techniques, analogous to those known in the art and particularly as illustrated in the examples or analogous to those illustrated in the examples hereinafter. The starting materials are readily available, are known, or can be prepared by known methods.

Under certain circumstances it is necessary to protect either the N or O of intermediates II and III in the above noted process with suitable protecting groups which are known. Introduction and removal of such suitable oxygen and nitrogen protecting groups are well known in the art of organic chemistry; see for example, (1) "Protective Groups in Organic Chemistry," J. F. W. McOmie, ed., (New York, 1973), pp. 43ff, 95ff; (2) J. F. W. McOmie, *Advances in Organic Chemistry*, 3:191–281 (1963); (3) R. A. Borssonas, *Advances in Organic Chemistry*, 3:159–190 (1963); and (4) J. F. W. McOmie, *Chem. & Ind.*, 603 (1979).

Examples of suitable oxygen protecting groups are benzyl, t-butyldimethylsilyl, methyl, isopropyl, ethyl, tertiary butyl, ethoxyethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

For example, the compounds of formula II$_c$ may require H of the OH on the R₁ and R₂ containing phenyl to be replaced by a protecting group for the reaction shown in the Scheme III and then reacted and deprotected to give compounds of formula I$_c$.

The products of the reactions described herein are isolated by conventional means such as extraction, distillation, chromatography, and the like. Generally, the starting materials are known, can be purchased commercialy, or synthesized by known methods.

The present invention is also a pharmaceutical composition for treating disease conditions comprising an effective amount for treatment of the disease of a compound of formula I and nontoxic, pharmaceutically acceptable base or acid addition salts thereof together with a pharmaceutically acceptable carrier.

Particularly, the present invention is a pharmaceutical composition for treating pain or inflammation, for example, headache, comprising an analgesic or antiinflammatory and also an antiheadache effective amount of the compound I or salts thereof as defined above and a pharmaceutically acceptable carrier.

The present invention is also a method of treating disease conditions, for example, pain and inflammation, comprising administration of a compound of formula I or a salt thereof as defined above to a mammal, including a human suffering therefrom in unit dosage form.

The compositions of the present invention may be one of a broad range of known forms for topical or systemic administration.

The methods of use are for the treatment in mammals, particularly in humans, of various conditions such as enumerated above either for diseases known as inflammatory or for pain. An ordinarily skilled physician would recognize such conditions. The compounds of formula I are active in animal tests which are generally recognized as predictive for antiinflammatory or analgesic activity. Regardless of the route of administration selected, the compounds of the present invention are formulated into pharmaceutically acceptable dosage forms by conventional methods known to the pharmaceutical art. In general a preferred method of administration is, however, by oral dosage form.

The compounds can be administered in such unit oral dosage forms as tablets, capsules, pills, powders, or granules. They may also be administered transdermally as patches, rectally or vaginally in such forms as suppositories or bougies, and occularly or nasally in the form of drops or aerosol. They may also be introduced parenterally, (e.g., subcutaneously, intravenously, or intramuscularly). The forms of each of these methods of administration are those known to the pharmaceutical art.

An effective but nontoxic amount of the compound of formula I or the salts thereof is employed in treatment. The dosage regimen for treating inflammation or pain by the compounds of formula I and their salts as described above is selected in accordance with a variety of factors including the type, age, weight, sex, and medical condition of the subject, the severity of the inflammation or pain, the route of administration and the particular compound employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

Initial dosages of the compounds of the invention are ordinarily in the area of 0.1 mg/kg up to at least 100 mg/kg per dose orally, preferably 1.0–30 mg/kg orally are given. Each dose is given from one to four times daily or as needed. When other forms of administration are employed equivalent doses are administered.

Illustrative examples of the activity for use as described above for the novel compounds of the present invention are shown as the compound of the noted examples described in the following material when administered in a test based on that of Koster et al. [Fed. Proc., Vol. 18 (1959), p. 412] in which the peritoneal injection of acetic acid to mice provokes repeated stretching and twisting movements which persist for more than six hours. Analgesics prevent or suppress these syndromes which are considered to be an exteriorization of a diffuse abdominal pain. A 1% solution of acetic acid in water is used at a dose of 0.01 ml/g or 100 mg/kg of acetic acid to release the syndrome.

The compound to be tested is subcutaneously administered 30 minutes before the acetic acid injection and the mice are fasted 24 hours before the start of the test. The stretching for the mice is observed and totaled for each mouse in a 15 minute observation period starting just after the acetic acid injection. The results are expressed as mg/kg which amount produces the desired inhibition of stretching or "writhing" in 50 percent of a population.

TABLE

| Example | $ED_{50}$ mg/kg |
| --- | --- |
| 1 | 6.1 |
| 2 | 2.5 |
| 3 | 3.2 |

The following examples will further illustrate the invention, without limiting it thereto.

EXAMPLE 1

Benzeneacetamide, 3-Chloro-4-hydroxy-N-octyl-

To a solution of 2.61 g 1,1'-carboxyldiimidazole (CDI) in 60 ml of anhydrous tetrahydrofuran (THF) is added, dropwise, a solution of 3-chloro-4-hydroxyphenylacetic acid (3.00 g) in 20 ml THF under $N_2$. The reaction solution is stirred for 30 minutes at room temperature following the addition and then refluxed for 30 minutes under N2 When the reaction solution is cooled to room temperature, a solution of 2.7 ml octylamine in 5 ml THF is added dropwise, and the resulting reaction solution is allowed to stir overnight at room temperature under $N_2$. After evaporation the reaction mixture is partitioned between 1N HCl and $CH_2Cl_2$. The $CH_2Cl_2$ layer (100 ml) is washed with 50 ml portions of 1N HCl, $H_2O$, saturated $NaHCO_3$, $H_2O$, and brine. The resulting product is flash chromatographed over 230–400 silica gel eluting with hexanes/ethylacetate (3:2) to yield benzeneacetamide, 3-chloro-4-hydroxy-N-octyl-, in a yield of 2.18 g (45.5%) mp 81°–82° C.

Calcd. C, 64.52; H, 8.12; N, 4.70; Cl, 11.91;
Found C, 64.81; H, 8.25; N, 5.09; Cl, 11.70.

EXAMPLE 2

Benzeneacetamide, 3-Bromo-4-hydroxy-N-octyl-

In a manner analogous to that described above in Example 1 using appropriate starting materials the desired product, benzeneacetamide, 3-bromo-4-hydroxy-N-octyl- is prepared in a yield of 2.11 g (47.5%) mp 85°–87° C.

Calcd. C, 56.14; H, 7.07; N, 4.09; Br, 23.35;
Found C, 56.42; H, 7.06; N, 4.28; Br, 22.99.

EXAMPLE 3

Benzeneacetamide, 3-Fluoro-4-hydroxy-N-octyl-

In a manner analogous to that described above in Example 1 using appropriate starting materials the desired product, benzeneacetamide, 3-fluoro-4-hydroxy-N-octyl- is prepared in a yield of 2.42 g (48%) mp 69°–71° C.

Calcd C, 68.30; H, 8.60; N, 4.98; F, 6.75;
Found C, 68.03; H, 8.55; N, 4.97; F, 7.01.

We claim:

1. A compound having a formula $I_1$ wherein $R_1$ is halogen or trifluoromethyl, X and Y are hydrogen and $R_3$ is alkyl of $C_8$–$C_{18}$ optionally substituted by $OR^1$, $CO_2R'$, $CONR'R''$, naphtyl, or tetrazolyl wherein R' and R'' are independently hydrogen or lower alkyl.

2. A compound of claim 1 wherein $R_3$ is alkyl of $C_8$–$C_{18}$.

* * * * *

UNITED STATES PATENT AND TRADEMARK OFFICE
CERTIFICATE OF CORRECTION

PATENT NO. : 5,220,064
DATED : June 15, 1993
INVENTOR(S) : Graham Johnson, etal

It is certified that error appears in the above-indentified patent and that said Letters Patent is hereby corrected as shown below:

Column 8, line 50, change "naphtyl" to --naphthyl--.

Signed and Sealed this

First Day of March, 1994

Attest:

BRUCE LEHMAN

Attesting Officer

Commissioner of Patents and Trademarks